United States Patent [19]
Greenberg

[11] Patent Number: 5,746,743
[45] Date of Patent: May 5, 1998

[54] SINGLE-HANDED SURGICAL DRILL DEPTH GUIDE WITH MANDIBULAR RETRACTOR

[75] Inventor: Alex M. Greenberg, New York, N.Y.

[73] Assignee: Greenberg Surgical Technologies, LLC, New York, N.Y.

[21] Appl. No.: 300,707

[22] Filed: Sep. 2, 1994

Related U.S. Application Data

[63] Continuation-in-part of Ser. No. 919,783, Jul. 24, 1992, Pat. No. 5,409,493, which is a continuation-in-part of Ser. No. 719,178, Jun. 21, 1991, Pat. No. 5,133,720, which is a continuation-in-part of Ser. No. 552,703, Jul. 13, 1990, Pat. No. 5,026,376.

[51] Int. Cl.⁶ ............................................. A61F 17/00
[52] U.S. Cl. ........................ 606/96; 606/86; 600/210; 600/215
[58] Field of Search ........................... 606/96, 86, 79, 606/80, 87, 97, 98, 102, 104; 600/190, 201, 210, 215, 235, 237, 238, 242

[56] References Cited

U.S. PATENT DOCUMENTS

| | | |
|---|---|---|
| 2,427,128 | 9/1947 | Ettinger . |
| 2,494,229 | 1/1950 | Collison . |
| 3,530,860 | 9/1970 | Majoros . |
| 3,752,161 | 8/1973 | Bent . |
| 3,835,860 | 9/1974 | Garretson . |
| 3,897,786 | 8/1975 | Garnett et al. . |
| 3,913,584 | 10/1975 | Walchle et al. . |
| 4,586,497 | 5/1986 | Dapra et al. . |
| 4,708,193 | 11/1987 | Dunbar . |
| 4,739,751 | 4/1988 | Sapega et al. . |
| 4,813,407 | 3/1989 | Vogen . |
| 4,883,048 | 11/1989 | Purnell et al. . |
| 5,013,318 | 5/1991 | Spranza . |
| 5,026,375 | 6/1991 | Linovitz et al. . |
| 5,026,376 | 6/1991 | Greenberg . |
| 5,133,720 | 7/1992 | Greenberg . |
| 5,197,967 | 3/1993 | Wilson . |
| 5,409,493 | 4/1995 | Greenberg ........................ 606/96 |
| 5,558,622 | 9/1996 | Greenberg ........................ 600/237 |

FOREIGN PATENT DOCUMENTS

| | | |
|---|---|---|
| 645252 | 7/1962 | Canada . |
| 2598311 | 11/1987 | France . |
| 2903-471 | 1/1978 | Germany . |
| 649420 | 7/1975 | U.S.S.R. . |

OTHER PUBLICATIONS

Oral and Maxillofacial Traumatology, "Internal Fixation of Zygomatic and Midface Fractures By Means of Mini Plates and Lag Screws", pp. 177–186 Quintessence Publishing Co., Inc. 1986.

"Summary of Surgical Technique" Catalog from Synthes Maxillofacial, Paoli, Pennsylvania (1992).

Walter Lorenz Surgical Instruments, Inc. Catalog pp. 213, 245, 250, 252–257, 259–261, and 263 (1993).

*Primary Examiner*—Robert A. Hafer
*Assistant Examiner*—Benjamin K. Koo
*Attorney, Agent, or Firm*—Meltzer, Lippe, Goldstein, et al.

[57] ABSTRACT

A surgical drill guide and retractor for treating mandibular fractures includes an adjustable length sleeve having an inner segment slidably mounted within an outer segment. The adjustable length sleeve also has a through-going lumen which connects a first opening at an end of the outer segment with a second opening at an end of the inner segment. The lumen is dimensioned for slidably receiving a drill bit or other instrument therein. A handle slidably retracts the inner segment into the outer segment to expose a preselected length of a drill bit or other instrument inserted through the lumen of the sleeve. A proximal end of the drill guide includes a mandibular retractor which is inserted intraorally or extraorally and has a retractor blade shaped to retract the cutaneous region laterally away from the bone. The retracting blade also has an aperture which allows surgical instruments to be inserted through the aperture to the bone. The retractor allows a surgeon to retract with one hand and view the surgical site. The surgeon's other hand is free to operate surgical instruments such as a drill or screwdriver.

16 Claims, 13 Drawing Sheets

5,746,743

SINGLE-HANDED SURGICAL DRILL DEPTH GUIDE WITH MANDIBULAR RETRACTOR

This is a continuation-in-part of application Ser. No. 07/919,783, filed Jul. 24, 1992, now U.S. Pat. No. 5,409,493, which is a continuation-in-part of application Ser. No. 07/719,178, filed Jun. 21, 1991, now U.S. Pat. No. 5,133,720, which is a continuation-in-part of application Ser. No. 07/552,703, filed Jul. 13, 1990, now U.S. Pat. No. 5,026,376. The contents of these applications and patents are incorporated by reference as if set out here in full.

FIELD OF THE INVENTION

The present invention relates to a combination surgical drill guide and mandibular retractor which may be adjusted and operated with a single hand. More particularly, the invention relates to a surgical instrument which acts as a drill depth guide and retractor for the reduction and fixation of a mandible.

BACKGROUND OF THE INVENTION

The treatment of bone fractures in craniomaxillofacial regions generally proceeds by reducing the fractured bone to its anatomically correct position, and thereafter fixing the bone in place. This procedure is known as an open reduction/internal fixation or "ORIF". In an ORIF, the bone may be fixed in place either by interosseous wiring, or by the technique of miniplate (or bone plate) osteosynthesis. See Greenberg, A. M., editor *Craniomaxillofacial Fractures: Principles of Internal Fixation Using the AO/ASIF Technique*, Springer Verlag, N.Y. (1993). In either case, holes must be drilled into the bone for receiving the interosseous wire or screws for holding the bone plates to the bone.

FIG. 1 shows a fractured mandible. The mandible M has a fracture F. The patient's skin S is shown in cutaway view. The mandibular nerve N runs through the mandible M and exits into the skin at an anterior position of the mandible where it becomes the mental nerve ME. The fractured mandible is treated with an ORIF procedure. The present invention is explained with respect to bone plate osteosynthesis of the mandible, but a person skilled in the art will readily understand that the disclosure is equally applicable to interosseous wiring and other procedures and to bones other than the mandible.

FIGS. 2 and 2A show a greatly enlarged bone plate P useful in the treatment of mandibular fractures by bone plate osteosynthesis. Numerous different configurations of the bone plate may be used depending on the size and shape of the fracture and bone structure to be reduced. The bone plate P is just one example of a suitable bone plate. The bone plate P consists of a chain-like body 20 having holes 22 therein. Each of the holes 22 is countersunk with a beveled edge 23 so that the holes 22 are adapted to receive surgical screws (not shown) and to retain the reduced bone in place until the bone heals. The bone plate holds the bone structure together so that it can heal.

An exemplary prior art intraoral (i.e., through the mouth) mandibular ORIF procedure is described as follows. As shown in FIG. 3A, a mandible M has a fracture F. The patient's skin S and tongue T are also shown. An incision SI is made through the patient's cutaneous region near the fracture F. A second incision, referred to here as the oral incision OI, is made in the buccal vestibule. The oral incision OI is generally V-shaped and (2) holding the plate in place on the tissue below; or (3) sitting the plate on the retractor's base. The surgeon then inserts a cannula or trocar T into incisions SI, OI into alignment with a hole in the bone plate P. Once aligned, the surgeon inserts a drill through a lumen in the trocar and drills a hole into the bone. The drill is removed and then a screw is screwed into the hole in the bone plate P, thus, affixing the bone plate P to the mandible M. Alternatively, a threaded opening may be tapped in the bone prior to the introduction of the screw. In such a case, a tap is applied to the hole drilled into the bone before the screw is applied. At least one screw is placed on each side of the fracture in order to stabilize the bone. No retractor is located behind the mandible during the fixation.

A mandibular ORIF procedure may also be performed extraorally, where access to the mandible is obtained entirely through an incision in the patient's cutaneous region. An extraoral procedure is particularly suitable for fractures in the posterior region of the mandible. This is because the patient's cheek may make an intraoral approach difficult or impossible.

When drilling holes into the bone structure, great care must be taken to ensure that the holes are drilled at precisely the correct place and to precisely the correct depth. If the holes are not drilled at the correct location, strain may be transmitted by screws to the surrounding bone structure. This may cause the bone to resorb in the vicinity of the screws resulting in loosening of the hardware. Similarly, complications could result if the depth of holes is not gauged accurately. For example, drilling too deeply or in the wrong location could damage mandibular nerve, the mental nerve, and/or other adjacent vital soft tissues. Accordingly, it is desirable during the drilling procedure to use an instrument which will prevent the surgeon from drilling too deeply into the mandible.

The procedure described above requires three or more "hands" to perform. Two hands are needed to retract the surgical site and the surgeon's hands are occupied with the trocar T or drill depth guide and the drill, tap, or screwdriver. Additional hands may be needed to hold the plate P in position. This is disadvantageous for several reasons. First, the anterior and posterior retraction limits the surgeon's view of and access to the surgical site. Second, "hands", instruments, and obstacles in the area of the surgical site (here, at least two hands are needed to hold the retractors) reduce the surgeon's already limited visibility of the surgical site. Third, a surgical assistant is needed. Surgical assistants are relatively costly to the patient. Many insurance companies are searching for ways to reduce the expense of surgical assistants and some have eliminated insurance payments for the assistant altogether for certain procedures, leaving the expense of the assistant to the patient.

The prior art drill guides and retractors and related surgical methods, while useful, are not entirely satisfactory for the procedure described above. A prior art drill guide for controlling the angle and the depth of a hole drilled into anatomical bone is disclosed in a catalog published in 1992 by Synthes Maxillofacial, a surgical supply company located in Paoli, Pa. This drill guide 30 is depicted in FIG. 4. The drill guide 30 has a threaded inner sleeve 32 which is screwed into a first opening 34a of an outer sleeve 34. By rotating the inner sleeve 32 with respect to the outer sleeve 34, the inner sleeve 32 may be extended from, or retracted into, the outer sleeve 34. A knurled nut 33 is provided which may be loosened to permit the rotation of the inner sleeve 32. After the inner sleeve 32 is adjusted to a desired length from the outer sleeve 34, the knurled nut 33 may be tightened to prevent rotation of the inner sleeve 32. The length is adjusted so that only a desired portion of a drill bit 36 extends beyond a proximal end of inner sleeve 32 when a quick coupling (or "chuck") 37 of a drill 38 is contacting a distal end of the outer sleeve 34. The outer sleeve 34 is attached to, and integral with, a handle 35. The outer sleeve 34 and handle 35 are connected so as to form an obtuse angle.

This drill depth guide requires more than one hand to adjust the drilling depth. One hand turns the knurled nut or inner sleeve and one hand grasps the drill guide handle. The drill guide does not include a retractor and therefore at least one additional hand is needed to retract.

Accordingly, it is an object of the present invention to provide a surgical instrument which will act as a drill guide and retractor for drilling and retracting mandibles and which can be operated with a single hand.

It is a further object of the present invention to provide a drill depth guide and retractor which reduces or eliminates the role of a surgical assistant in a mandibular ORIF procedure.

It is yet a further object of the invention to provide a drill depth guide and retractor which allows a surgeon to reduce the mandible, retract and view the surgical site, hold a bone plate in position, and operate a drill depth guide with one hand, leaving the other hand free to operate surgical instruments.

It is yet another object of the present invention to provide a drill depth guide and retractor having a retractor with an aperture so that the retractor retracts a lateral aspect of the oral incision and permits the drill depth guide and other surgical instruments to access the surgical site.

It is yet a further object of the invention to provide a drill depth guide and retractor where a retractor portion may be selectively moved superiorly and inferiorly with respect a drill depth guide portion for use in the posterior region of the mandible.

It is yet a further object of the invention to provide a drill depth guide and retractor having a retractor blade that rotates radially.

It is yet another object of the invention to provide a drill depth guide and retractor having an arched arm connected to retractor blade to operate as a stabilizing arm. The arched arm may optionally be moveably anteriorly and posteriorly with respect to a proximal end of the drill guide.

It is yet another object of the present invention to provide a drill guide which can limit the drilling of holes to depths less than or equal to the entire thickness of the bone.

SUMMARY OF THE INVENTION

The present invention achieves these and other objects by providing a surgical drill guide and retractor having a handle from which a substantially L-shaped member extends. Mounted on the member is a plunging mechanism comprising outer and inner sleeves. The inner sleeve is longitudinally slidable within a lumen of the outer sleeve. The inner sleeve may be retracted or expanded though the lumen of the outer sleeve to contact a bone plate. When the inner sleeve contacts the bone plate, markings on the inner sleeve enable the surgeon to gauge the length of a hole to be drilled in a mandible.

A distal end of the member includes a mandibular retractor. The curvature of the retracting blade is designed to retract a lateral aspect of an oral incision. The retractor also has an arcuate tip which is shaped to fit under and behind the mandible. An aperture defined in the retractor blade allows the inner sleeve to extend through the retractor towards the mandible. The retractor may also include a bone plate carrying shelf located proximally of the aperture. The shelf is shaped to conform snugly to a bone plate. This device may be used for either an intraoral or extraoral procedure.

Another embodiment of the surgical drill guide and retractor according to the present invention has an adjustable length sleeve with an inner segment slidably mounted within an outer segment and a specially shaped tip for retracting the mandible. The retractor is designed to laterally retract the oral incision and to fit under and behind the mandible and has an aperture to allow the distal end of the sleeve to extend through and may be used in intraoral or extraoral procedures. The retractor may include a bone plate carrying shelf.

The adjustable length sleeve has a lumen which passes entirely through the inner and outer segments and which connects openings at the proximal and distal ends of the adjustable length sleeve. The sleeve is mounted to a handle having a trigger for retracting the inner segment into the outer segment, thereby exposing a preselected amount of a drill bit inserted through the sleeve. The lumen has a diameter dimensioned so that a drill bit or other instrument may be inserted through the adjustable length sleeve.

The length of the drill bit which can be extended beyond a distal end of the adjustable length sleeve may be limited to a particular length. For example, a drill bit may be inserted into an opening at a proximal end of the sleeve and through the lumen until the quick coupling (or "chuck") of the drill, to which the proximal end of the drill bit is attached, contacts the proximal end of the adjustable sleeve. Using the trigger, the inner segment may then be retracted to expose a preselected amount of the drill bit protruding from an opening at the distal end of the sleeve.

Illustratively, the trigger and handle are each connected to a different segment. In an embodiment, the trigger is pivotally connected to the handle for a scissoring movement therewith. Thus, when the trigger is urged towards the handle, the inner segment slides into the outer segment. In an alternative embodiment, the trigger and handle are not connected together. In this embodiment, the trigger may be urged towards the handle by a simple sliding movement to retract the inner segment into the outer segment.

The retractor allows a surgeon to retract and operate the drill depth guide with one hand. The surgeon's other hand is free to operate surgical instruments, such as a drill or screwdriver. No additional retractors are necessary, thus reducing the number of hands in the area of the surgery. Therefore, the surgical assistant's role is reduced or eliminated. Also, because the retractor retracts the oral incision laterally, the incision is pulled open and the surgeon has good visibility of the surgical site. In an intraoral procedure, the surgeon may view the surgical site by looking down into the patient's mouth.

The retractor portion may be demountably attached to the drill depth guide portion. This allows interchangeability of differently shaped retractor portions. Also, the retractor may be selectively moved superiorly and inferiorly with respect to the drill depth guide portion.

Another embodiment has an arched arm connected at one end to an outer sleeve of the drill depth guide and having at another end a retractor blade. Optionally, the arched arm may be slidably mounted to the outer sleeve to be moved anteriorly/posteriorly in relation to a distal end of the drill depth guide.

Optionally, a depth scale may be provided on the outer surface of the sleeve which may be used to calculate the drilling depth of the drill bit. Other options include a spring for biasing the sleeve to its fully extended position; a fastener, such as a set screw, for retaining the length of the sleeve in a fixed position during the drilling of holes; and a retractor blade that rotates radially.

BRIEF DESCRIPTION OF THE DRAWINGS

These and other objects and features of the invention will become apparent from the following drawings, wherein.

DETAILED DESCRIPTION OF THE INVENTION

Figure 5:
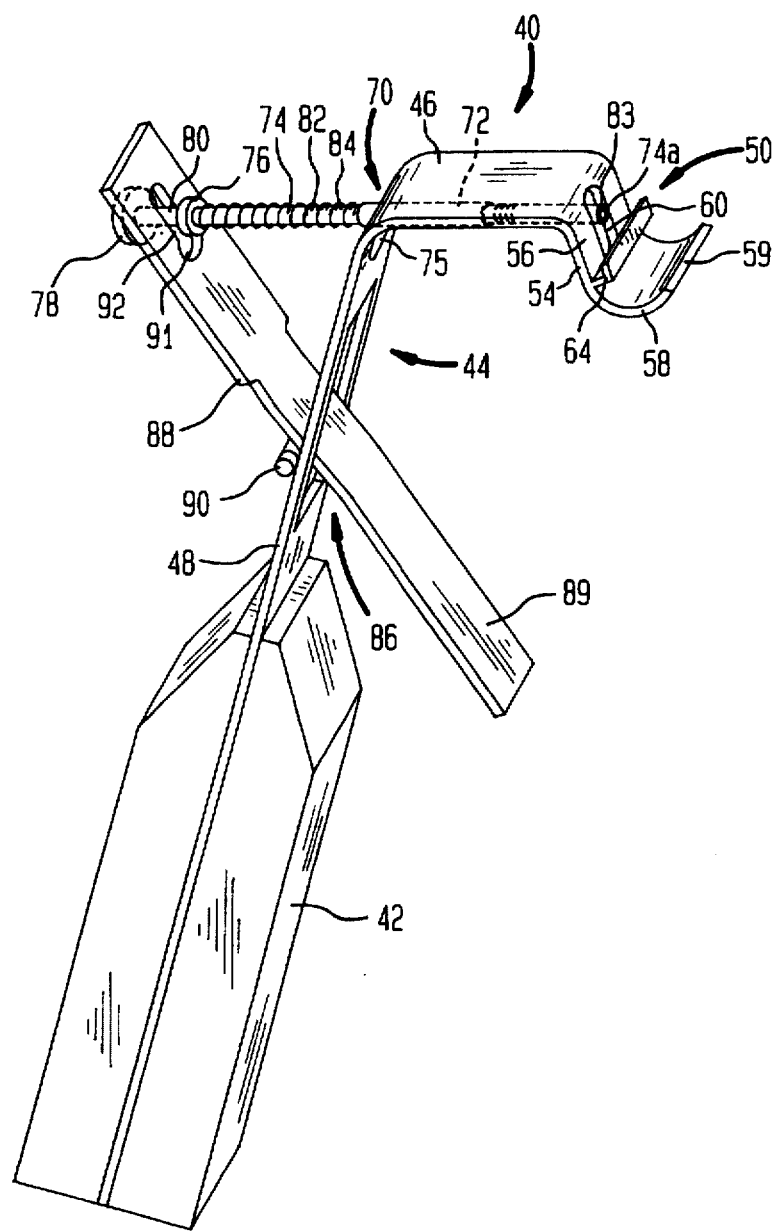
FIG. 5 is a side perspective view of one embodiment of the drill guide and retractor according to the invention.
Figure 6:
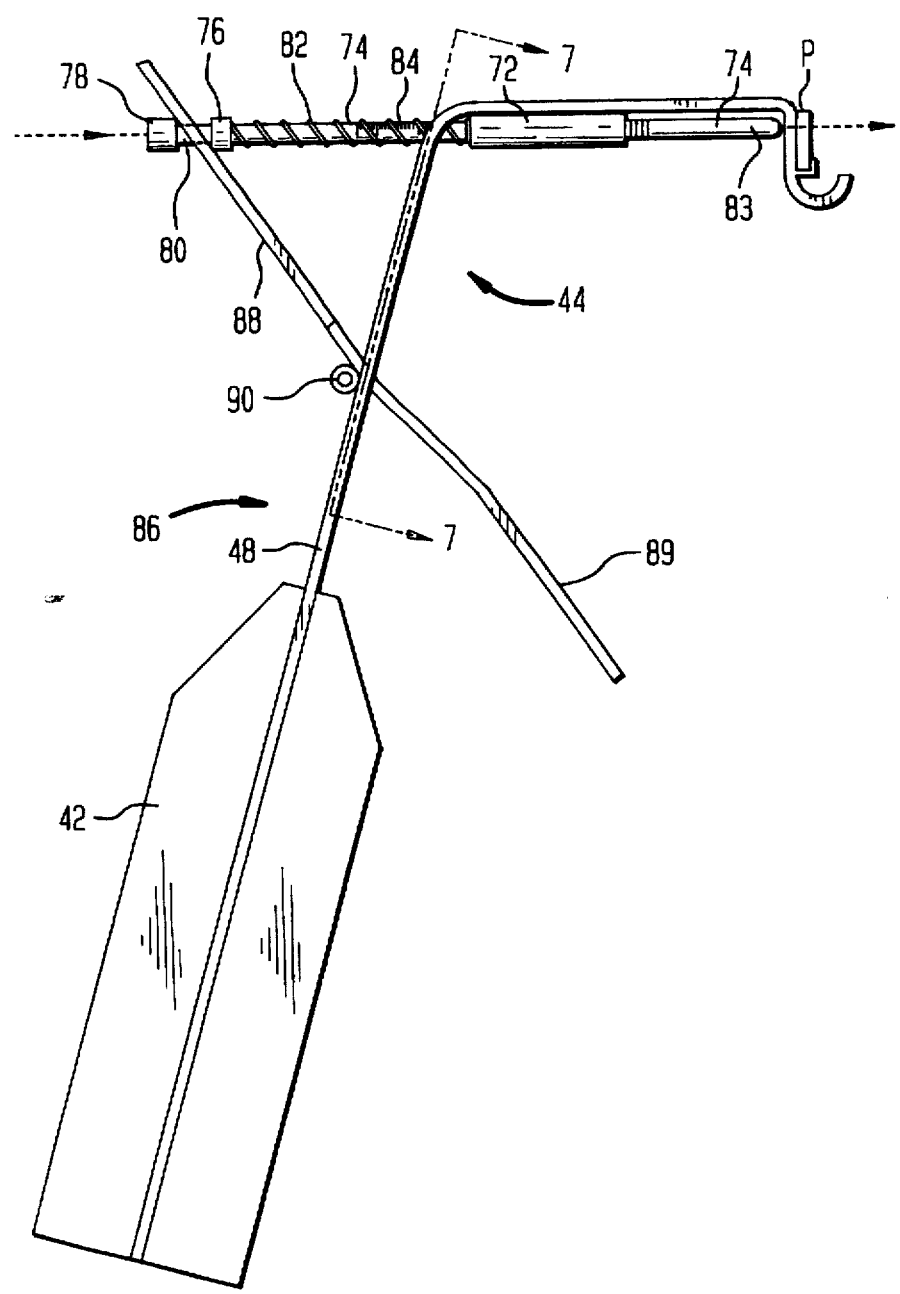
FIG. 6 is a side elevation view of the drill guide and retractor of FIG. 5.
Figure 7:
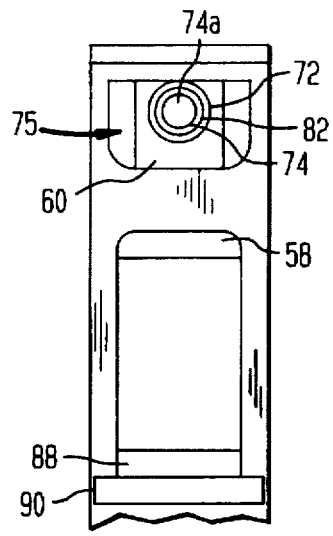
FIG. 7 is a partial cutaway view taken along lines 7—7 of the drill guide of FIG. 6.

Referring now to FIGS. 5, 6, and 7, an embodiment of the inventive surgical drill guide and retractor is illustrated. The surgical drill guide and retractor 40 comprises a handle 42 from which a substantially L-shaped member 44 extends. The L-shaped member has a first short leg 46 and a second long leg 48. The long leg 48 extends from handle 42.

Figure 17:
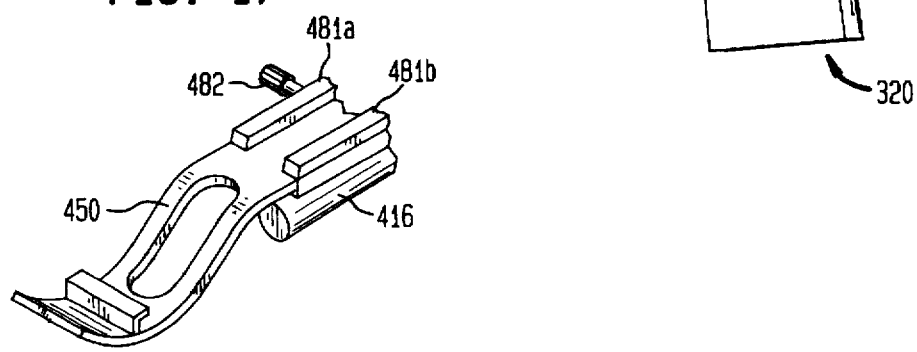
FIG. 17 is a perspective view of a demountable retractor blade according to the present invention.

The distal end of the short leg 46 terminates in a member which constitutes a mandibular retractor 50. In the embodiment shown in FIG. 5, the retractor 50 is integral with and extends from the short leg 46, although this need not be so. It may also be a separate piece which is attached to the short leg 46, as shown in FIG. 17. The retractor 50 includes a retracting blade 54 which comprises a curved portion 56 at the proximal end of the retractor blade 54, an arcuate portion 58 having a tip 59 at the distal end of the retractor blade 54, and an aperture 60 defined in the retracting blade 54 located proximally from the tip 59.

Figure 8:
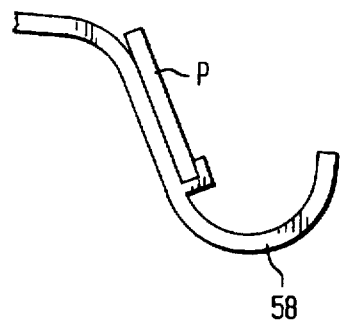
FIG. 8 is a side view of the retractor tip of the drill guide and retractor of FIG. 5 having a bone plate inserted.
Figure 8A:
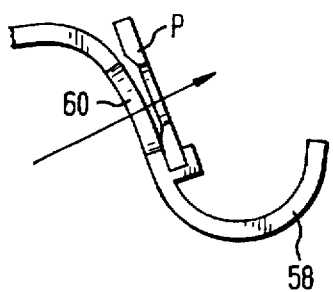
FIG. 8A is a partial cross sectional view of the retractor blade and bone plate of FIG. 8.
Figure 9:
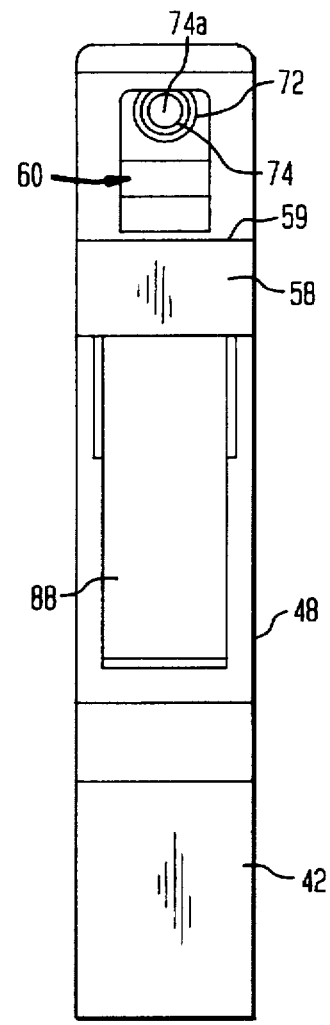
FIG. 9 is a front elevational view of the drill guide and retractor of FIG. 5.

The curvature of the retracting blade according to the present invention is designed allows retraction of the lateral aspect of the V-shaped oral incision, that is, in a direction generally perpendicular to the mandible. Retracting in this direction opens the V-shaped oral incision OI (see the arrow in FIG. 10). In an intraoral procedure, the retracting blade may be inserted into the patient's mouth and to hold the reduced mandible in place and retract the surgical site. The curved portion 56 has a long, gradual curvilinear shape. This curvature pulls the soft tissues in a direction away from the mandible sufficiently to allow observation of the surgical site. The arcuate tip 58 is generally semi-circular and is designed to fit under and behind the mandible. The tip 59 does not extend too far upwards, because it would be impeded by soft tissue. The retractor may also include a bone plate carrying shelf 64 located distally of the aperture 60. The shelf 64 is shaped to conform snugly to a bone plate P. As shown in FIG. 8, a bone plate P may be inserted into the shelf 64 before the retractor is placed at the surgical site. Thus, the shelf 64 operates as a carrier to locate the plate P at the fracture and holds it in place when the retractor 50 is positioned with respect to the mandible. The position of the shelf 64 between the tip 58 and the aperture 60 allows the bone plate holes 22 to align with the aperture 60. Thus, a straight line exists from the incision, through the retractor aperture 60 and the bone plate hole 22 to the mandible, as indicated by the arrow in FIG. 8A. Also, there is no need for additional assistants or surgical instruments to position or hold the plate against the mandible.

Figure 1:
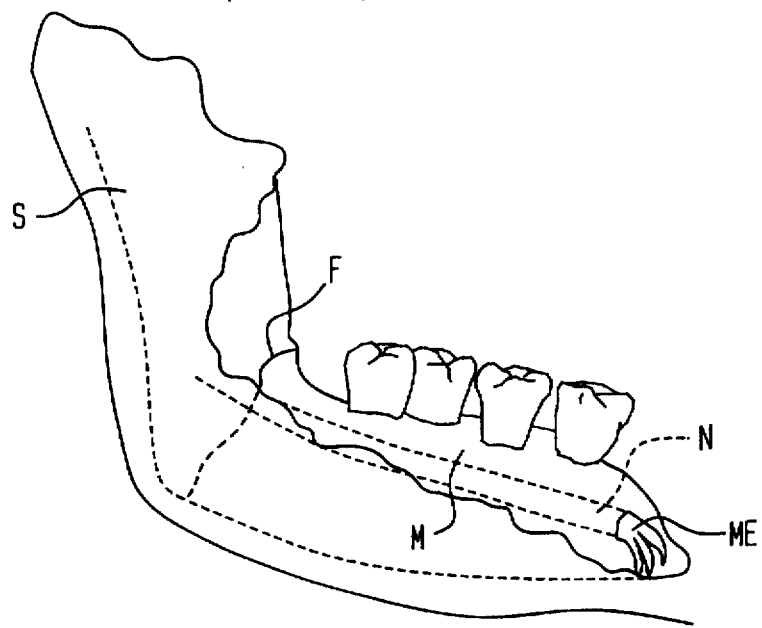
FIG. 1 illustrates a fractured mandible.
Figure 2:
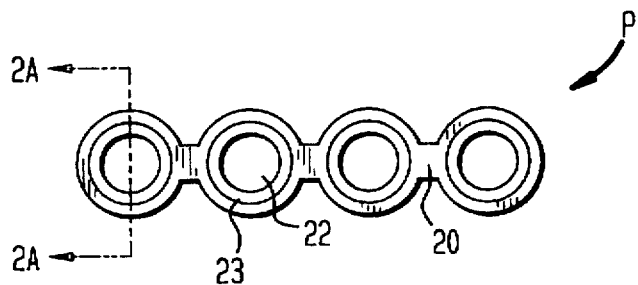
FIG. 2 illustrates a prior art bone plate for use in securing bone fragments together.
Figure 2A:
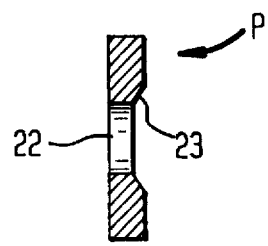
FIG. 2A is a cross sectional view of the bone plate of FIG. 2.
Figure 3A:
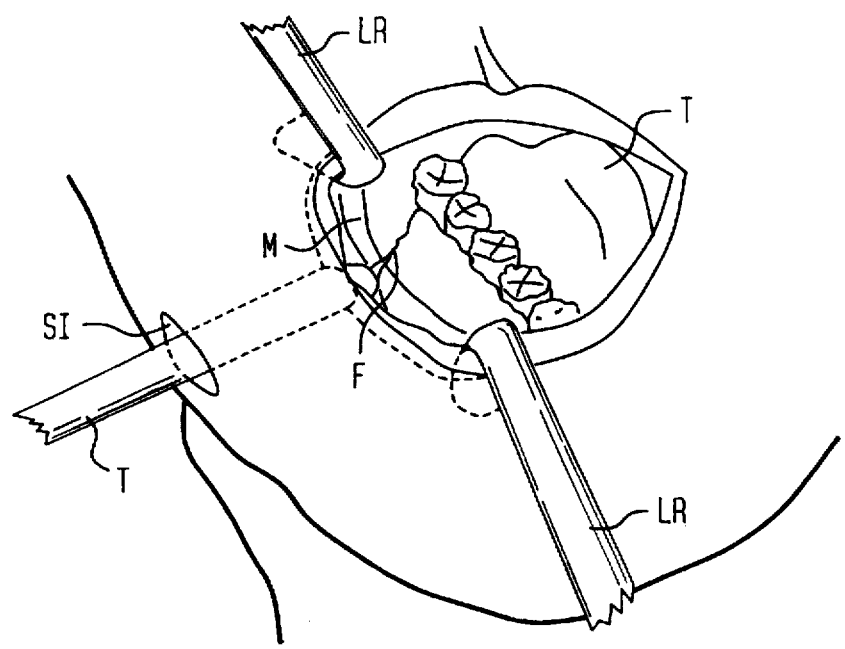
FIGS. 3A–3D illustrate a prior art intraoral ORIF procedure for the fractured mandible of FIG. 1.
Figure 3B:
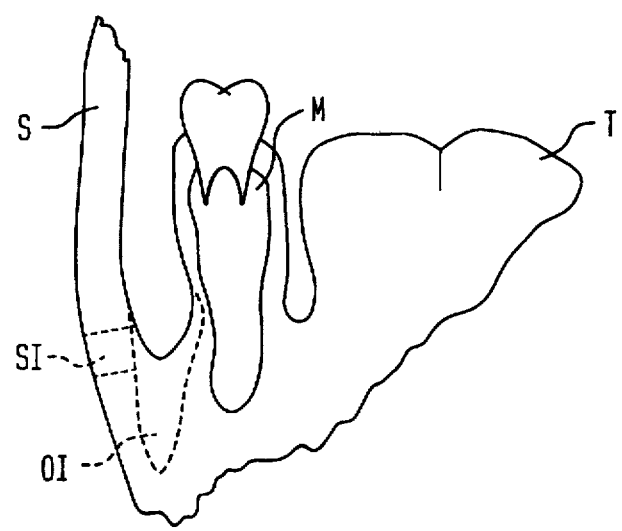
Figure 3C:
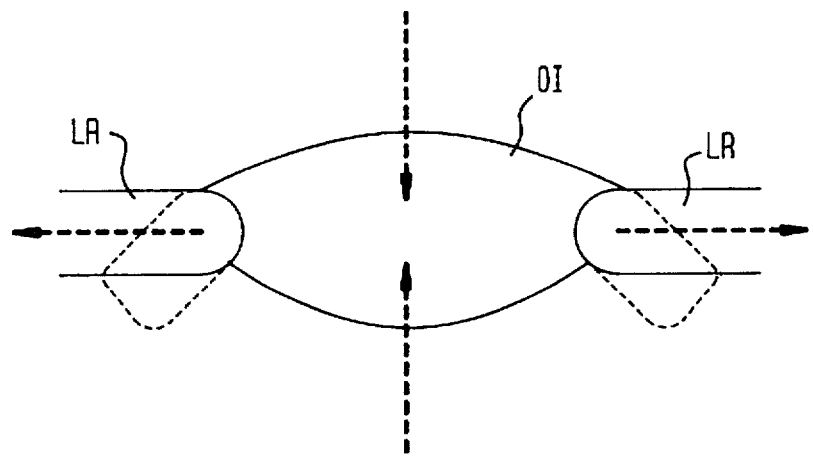
Figure 3D:
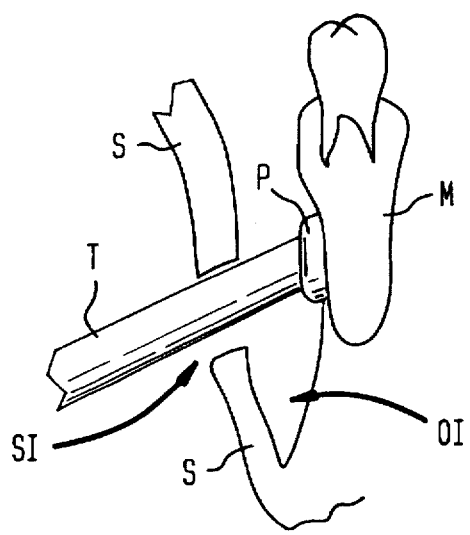
Figure 4:
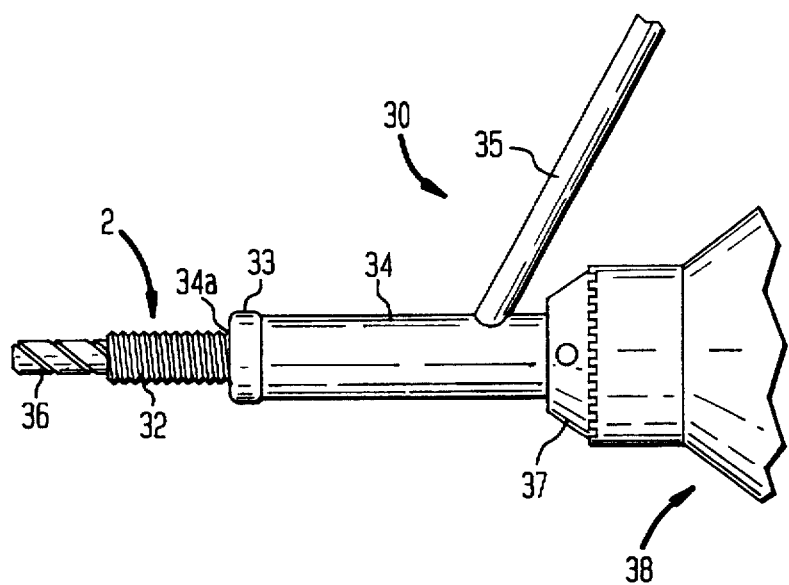
FIG. 4 illustrates a prior art drill guide.

Mounted under the short leg 46 is a plunging mechanism 70. The plunging mechanism 70 comprises an outer sleeve 72 and an inner sleeve 74. Each sleeve is cylindrical and has a through-going, longitudinal lumen. The inner sleeve 74 is slidable within the lumen of outer sleeve 72 to slide between a retracted and extended position in the longitudinal direction. The inner sleeve also extends through an opening 75 in the long leg 48. The inner sleeve lumen 74A has a diameter dimensioned for slidably receiving a surgical instrument, such as a drill bit. At a distal end of the inner sleeve are two circumferential shoulders 76 and 78 with a circumferential land 80 between them. A coil spring 82 is disposed against an edge of outer sleeve 72 and against the shoulder 76 connected to the inner sleeve 74 in order to resiliently bias the inner sleeve 74 into the retracted position shown in FIGS. 5, 6, and 7. At the distal end of inner sleeve 74, a tip 83 is chamfered so that it will register with edges 23 of the holes 22 of a bone plate (see FIG. 2). The barrel of the inner sleeve 74 is scored with markings 84 near the proximal end of the outer sleeve 62. When the inner sleeve 74 is extended to contact the bone plate, the markings 84 enable the surgeon to gauge the desired hole depth or length of screw required. Preferably, the markings indicate the distance from the retractor tip 59 which is located behind the mandible, to the inner sleeve tip 83, thus indicating the maximum hole depth or screw length.

A lever 86 having first and second lever arms 88, 89 is mounted via a hinge pin 90 on the long leg 48 of L-shaped member 44. The lever is hinged to the L-shaped member to provide a scissoring movement with the handle 42 and the inner sleeve 74 via hinge pin 90. The lever arm 88 contacts the land 80 of inner sleeve 74 with a hole 91 and slot 92 arrangement. The hinge pin 90 is preferably constructed in the form of a thumb screw so that it can be disassembled. When the second lever arm 89 is pulled towards the handle 42, the first lever arm causes the inner sleeve 74 to extend.

Figure 10A:
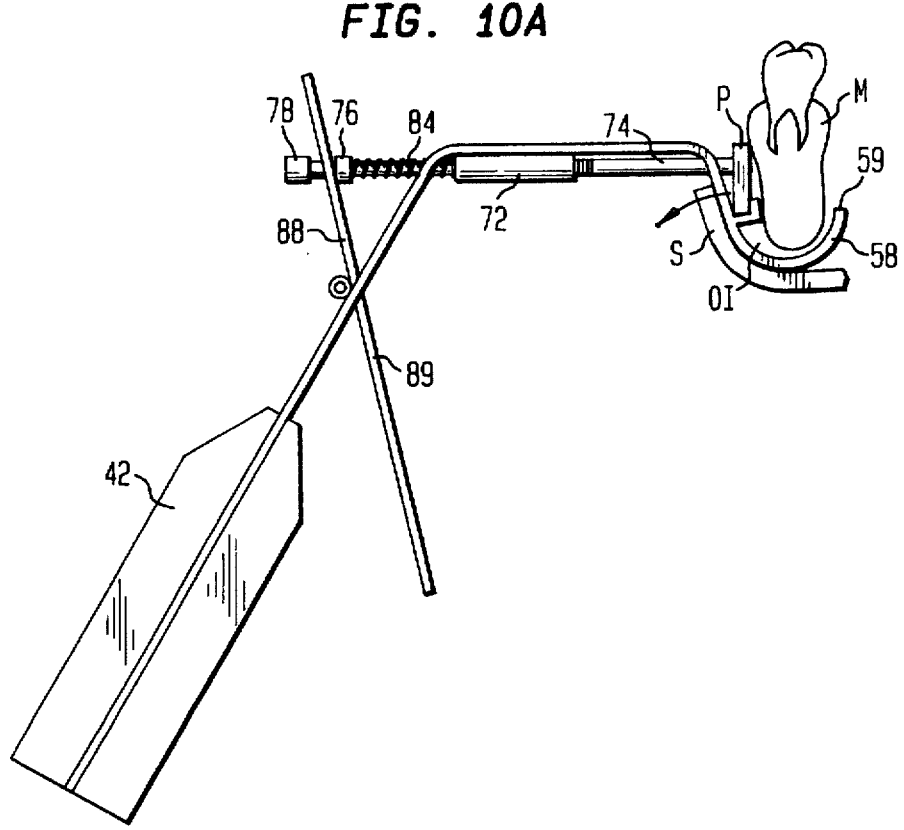
FIG. 10A illustrates the drill guide and retractor of FIG. 5 in use in an intraoral ORIF procedure.

FIG. 10A illustrates the drill depth guide and retractor 40 in use in an intraoral ORIF procedure. The intraoral ORIF procedure is particularly suitable for use with fractures at the anterior region of the mandible. It is more difficult to perform intraoral ORIF procedures for fractures at a posterior region of the mandible because the presence of the patient's cheek between the retractor 50 and the drill depth guide makes it difficult to align the drill guide tip 83 with the incision while retracting. A V-shaped oral incision OI are made in the region of the fracture F. The entire drill guide and retractor 40 is inserted into the patient's mouth and the arcuate portion 58 and tip 59 are manipulated through the oral incision OI to be positioned under and behind the fractured mandible M. The retractor is positioned so that the aperture 60 is aligned with the incision and the tip 83 of inner sleeve 74. The retractor is used to reduce the mandible M to its correct anatomical position. The patient's cutaneous region (skin S) may be retracted away from the mandible M in the direction of the arrow so that the surgeon may observe the surgical site by looking down into the patient's mouth. This retraction pulls the oral incision OI laterally, thus opening the oral incision OI, providing good visibility of the surgical site.

Figure 10B:
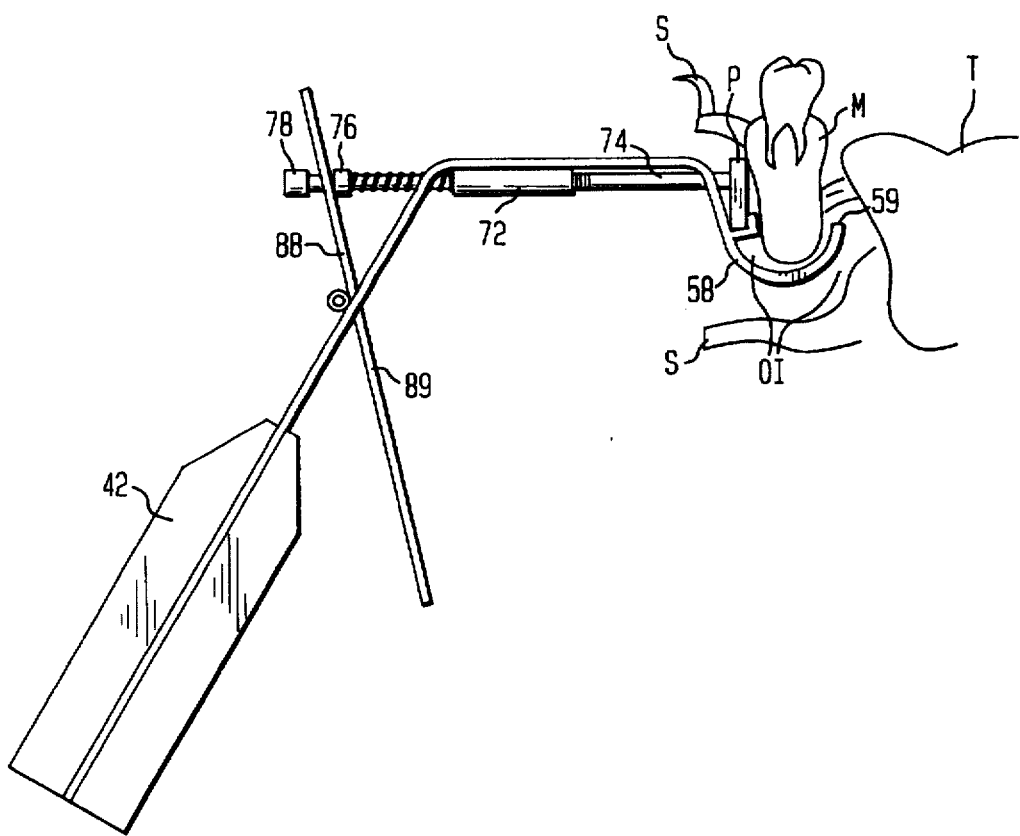
FIG. 10B illustrates the drill guide and retractor of FIG. 5 in use in an extraoral ORIF procedure.

FIG. 10B illustrates the drill depth guide and retractor 40 in use in an extraoral ORIF procedure. A skin incision SI and oral incision OI are made in the region of the fracture F. The retractor 50 is inserted through the both incisions and the arcuate portion 58 and tip 59 are manipulated to be positioned under and behind the fractured mandible M. The mandible M is reduced. The patient's skin and other soft tissues are held away from the surgical site by the retractor 50.

After reduction in either procedure, a bone plate P is positioned across the fracture in the conventional manner, or is already in place if it was preloaded onto shelf 64. With one finger, the surgeon pulls the second lever arm 89 so that it is brought into proximity with the handle 42. This causes the first lever arm 88 to press against the shoulder 76 and the inner sleeve 74 slides forward through the lumen of the outer sleeve 72 and through the aperture 60 of the retractor 50 until the tip 83 abuts against a hole of bone plate P.

Thus, with a single hand, the surgeon is able to retract the incision, brace the bone plate in place, and provide a drill guide. With the other hand, the surgeon now commences drilling by inserting a drill bit (not shown) through the lumen 74A of the inner sleeve 74 and drilling through the bone. After the drilling, the drill bit is withdrawn and a self-tapping surgical screw is inserted through the bore of the inner sleeve 74 and screwed through the bone plate P and the bone. Because the markings 84 on the inner sleeve 74 are calibrated against the distance to the tip 59 of retractor 50, the surgeon can easily determine the combined depth of the bone plate and the bone. This enables the surgeon to select a screw of the precise length required.

Figure 11:
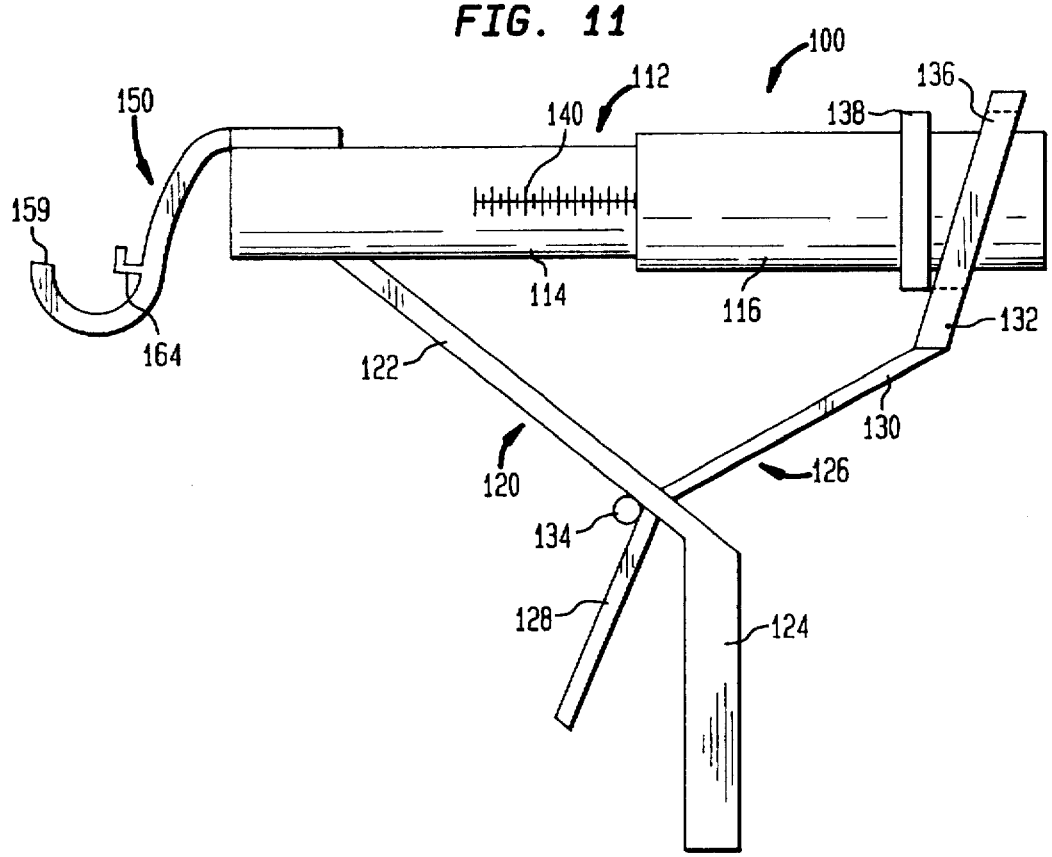
FIG. 11 is a side elevational view of another embodiment of the drill guide and retractor according to the present invention.
Figure 12:
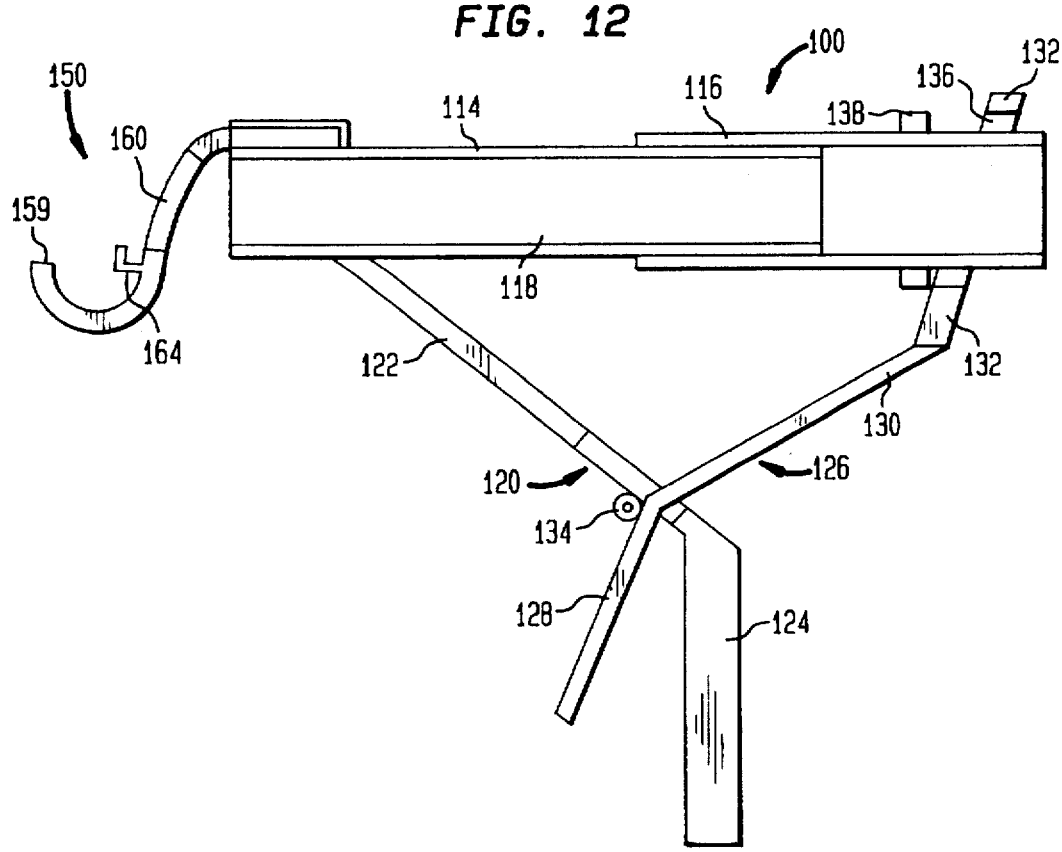
FIG. 12 is a side cutaway view of the drill guide and retractor of FIG. 11.
Figure 13:
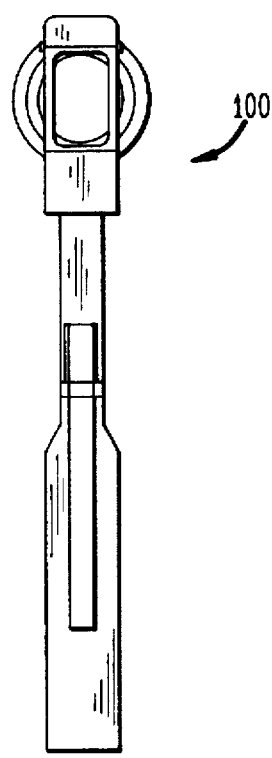
FIG. 13 is a front elevational view of the drill guide and retractor of FIG. 11.

A drill guide and retractor 100 according to another embodiment of the present invention is depicted in FIGS. 11-13. The drill guide 100 has an adjustable length sleeve 112 which includes an inner segment 114 and an outer segment 116, both segments having lumens. The inner segment 114 is positioned within the outer segment 116 and is retractably disposed with respect to the outer segment to slidably retract or extend therefrom. The length of the adjustable sleeve 112 varies depending on the position of the inner sleeve 74 with respect to the outer sleeve 72.

The lumens of the inner and outer sleeves 74, 72 align longitudinally so that sleeve 112 has a single lumen 118 which passes through both segments 114 and 116. The lumen 118 has a diameter dimensioned to receive a drill bit or other instrument therethrough.

As depicted, a handle 120 is connected to the inner segment 114. The handle 120 includes a member 122 which is connected to the inner segment 114 and to a grip 124. A segmented trigger 126 is also provided with a lever arm 128 attached to a connecting member 130 which is also attached to a contact plate 132. As shown in FIGS. 11 and 12, the lever arm 128 is illustratively connected to the member 122 by a hinge or pivot 134. The handle 120 and trigger 126 are thus capable of a scissoring movement.

The contact plate 132 has a slot 136 into which the outer segment 116 is positioned. The outer segment 116 also has a contact shoulder or ring 138 on its outer surface. The contact ring 138 has a diameter which is greater than the width of the slot 136 so that it cannot be inserted therein.

The distal end of drill guide and retractor 100 has a retractor 150 as described above. The retractor 150 may optionally include the bone plate carrying shelf 164.

As shown in FIG. 11, the inner segment 114 illustratively is scored with markings 140. These markings form a measuring scale or gauge useful in measuring the depth that a drill bit inserted through the sleeve 112 may penetrate into the bone.

Figure 14:
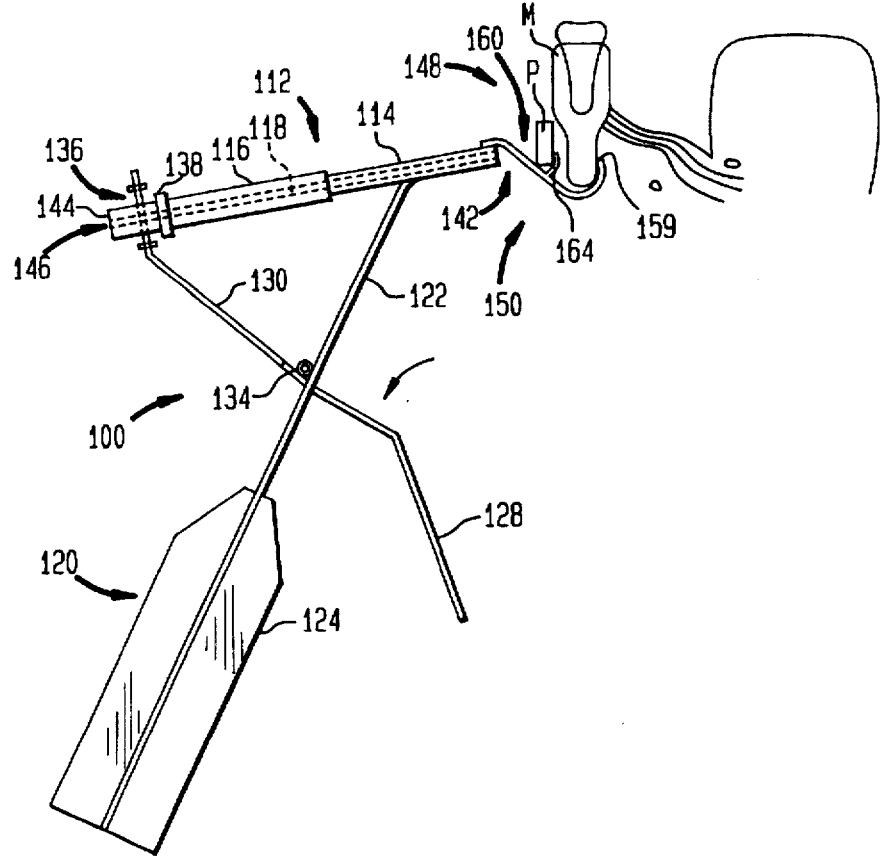
FIG. 14 illustrates the drill guide and retractor of FIG. 11 in use.

As seen in FIG. 14, the drill guide and retractor 100 may be used in the technique of bone plate osteosynthesis. As with the embodiment illustrated in FIGS. 5-11, this embodiment may be also used in either an intraoral or extraoral procedure. In either procedure, the desired incisions are made in the region of the mandibular fracture to which the bone plate 20 is to be secured. The surgeon then inserts the retractor portion 150 of the device 100 into the surgical site and positions tip 159 of the retractor 150 under the mandible and aligns the aperture 160 defined by of the retractor blade with the incision(s). The adjustable length sleeve 112 is located with distal end of the inner tube 114 aligned with the incision(s) and bone plate. The mandible is reduced to its correct anatomical position and the bone plate P is positioned on across the fracture, or, if the shelf 164 is present, the bone plate P is already properly positioned.

The surgeon grasps the drill guide 100 which has the lumen 118 having a diameter dimension for receiving a drill bit. While holding the drill guide 100 with one hand by its grip 124, the surgeon, using a finger, depresses the lever arm 128 so that it is brought into proximity with the grip 124. This causes the contact plate 132 to press against the contact ring 138 thereby retracting the inner segment 114 into the outer segment 116, thus changing the length of adjustable length sleeve 112. The surgeon continues to squeeze the lever arm 128 until the adjustable length sleeve 112 is the correct length, i.e., the length of the drill bit less the desired drilling depth.

The surgeon can utilize the markings 140 on the inner sleeve to determine the correct amount that the inner segment 114 should be retracted into the outer segment 116. Because the scored markings 140 on the barrel of inner sleeve 114 are calibrated against the overall length of the sleeve 112, the surgeon can easily determine the length of the drill bit protruding from the distal end 148 of the adjustable length sleeve 112 and thus, the depth of the hole. This allows the surgeon to drill a hole to a desired depth, thus avoid injury to the patient, for example avoiding drilling into the mandibular nerve. This gauge also enables the surgeon to select a screw of the precise required length. In addition, the drill guide 100 may be used for tapping or countersinking the hole prior to inserting the screw. In such a case, the appropriate instrument, e.g., tap, countersink, etc. may be inserted into the lumen 118 and thereby guided by guide 100.

Alternatively, the surgeon may insert a drill bit as far as possible (e.g., until the quick coupling, or chuck, of the drill contacts distal end 144 of the outer segment 116) into the opening 146. The surgeon then adjusts the length of the adjustable length sleeve 112 by measuring the exposed portion of the drill bit protruding from opening 142 at the distal end of the sleeve 112.

Next, the bone plate 20 is positioned across the fracture. If the retractor 150 includes bone plate carrying shelf 164, the bone plate 20 is already positioned across the fracture with one hand, the surgeon is retracting and operating the drill guide. With the other hand, the surgeon now commences drilling by inserting a drill bit (not shown) through the lumen 118 of the adjustable length sleeve 112 through the aperture 160 defined in the retractor, and through the hole 22 in the bone plate to contact the bone. The drilling proceeds until the quick coupling of the drill contacts the distal end of the adjustable length sleeve 112. Because the quick coupling has a larger girth than the drill bit or the lumen, the proximal end of the adjustable sleeve prevents the coupling from being inserted into the sleeve 112. Thus, only the distal portion of the bit protruding from distal end 148 of the adjustable length sleeve 112 can penetrate into the bone.

After the hole is drilled, the drill bit is withdrawn and a screw is inserted through the lumen 118 and screwed through the hole in the bone plate to secure the bone plate to the bone. When this entire procedure is completed for one hole, the surgeon moves to the next hole of the bone plate P and repeats the procedure until the bone plate P has been properly secured into position on the reduced bone structure. The inventive drill guide and retractor 100 may also be used in the technique of interosseous wiring.

This device has several advantages. First, the surgeon can retract, adjust the depth of the drill guide, and hold the drill simultaneously. Also, because the retractor retracts the lateral aspect of the oral incision, the incision is opened, providing the surgeon with good visibility of the surgical site, particularly in the intraoral procedure. Also, the number of obstructions involved is reduced. No additional retractors are needed, and the retraction and drill depth guide are operated with one hand and a second hand is free to operate a drill, screwdriver, or other surgical instrument. Thus, a first assistant may not be necessary. These advantages result in significant time and cost savings, both of which are important considerations.

Figure 15:
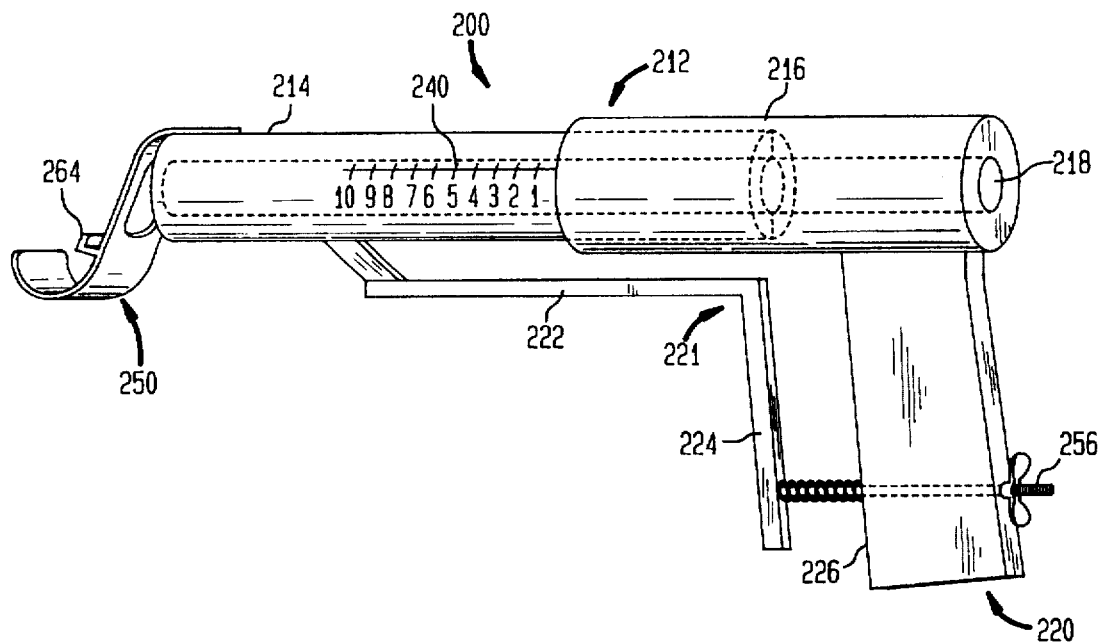
FIG. 15 is a side elevational view of another embodiment of the drill guide and retractor according to the present invention.

FIG. 15 illustrates another embodiment of the drill guide and retractor 250 according to the invention. In this embodiment, the handle 220 includes a grip 226 attached to the outer segment 216. The trigger 221 is an approximately L-shaped member having a long leg 222 attached to the inner segment 214 and a short leg 224 which extends in the vicinity of the handle 226. In this embodiment, the inner segment 214 may be retracted into the outer segment 216 by sliding the short leg 224 towards the handle 226. The drill guide 200 is also shown with a set screw 256 which is capable of retaining the inner segment 214 in its adjusted position while the surgeon operates the drill. In this case, the inventive instrument is self-retaining. In the alternative, a ratchet mechanism can be used for adjusting the length of the sleeve 212 and for retaining the inner segment 214 in its adjusted state. Connected to the inner segment 214 is a retractor 250. The retractor has the same shape as described above in relation to FIGS. 8 and 8A, and may also include a bone plate carrying shelf 264.

Figure 16:
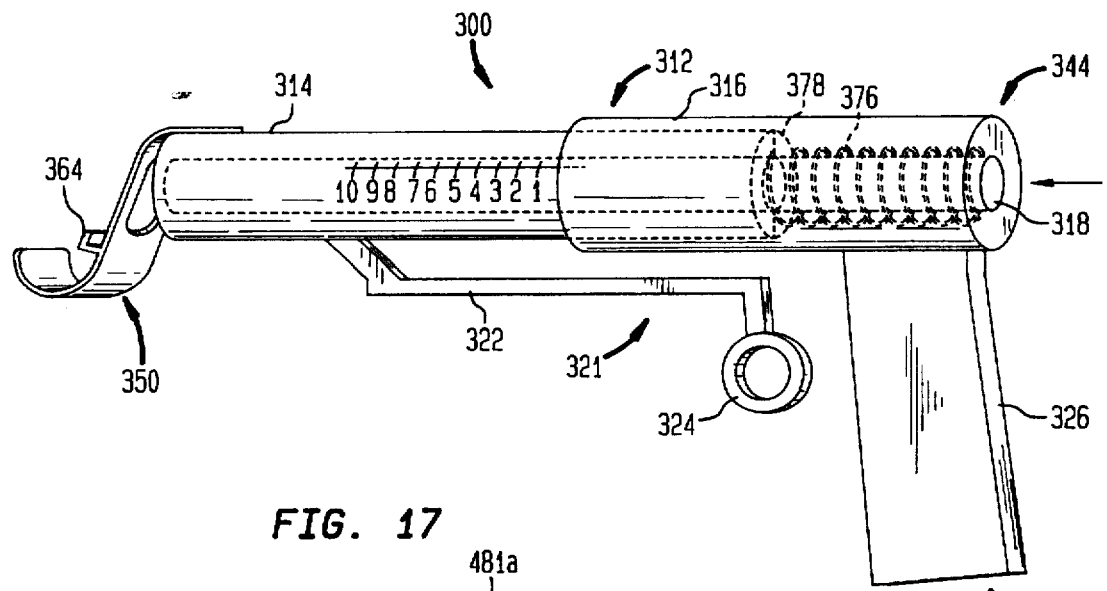
FIG. 16 is a side elevational view of another embodiment of the drill guide and retractor according to the present invention.

FIG. 16 illustrates yet another embodiment of the drill guide and retractor 300 according to the invention. This embodiment is similar to that shown in FIG. 15 with several additional features. The drill guide 300 shown in FIG. 16 has a trigger 321 which includes a long member 322 connected to the inner segment 314 and extending towards the handle grip 326. An eyelet 324 is formed at the end of this member 322 which makes it easier to retract the inner segment 314 using a single finger. The drill guide 300 is also shown with a spring 376 positioned within the outer segment 316. As shown, the spring 376 is a helical compression spring positioned between the inner side of the proximal end 344 of the adjustable length sleeve 312 and distal end 378 of the inner segment 314. The spring 376 biases the inner segment 314 into its extended position. Connected to a distal end of the adjustable length sleeve 312 is a retractor 350. The retractor 350 has the same shape as described above in relation to FIGS. 8 and 8A, and may also include a bone plate carrying shelf 364.

In all of the embodiments described above, the retractor may be either permanently or demountably attached to the distal end of the drill guides. As seen in FIG. 17, a retractor blade 450 is provided at the end of a short leg 416 and is demountably attached to the short leg 416 by screws or by means of some other similar fastener. In this illustrative embodiment, the retractor blade 450 slides between C-shaped clamps 481A and 481B and may be adjusted to a desired extension from the short leg 416 and then secured by the knurled screw 482. A person skilled in the art recognizes that the retractor blade 450 may be demounted in any number of ways. The demountable retractor blade may be interchanged with differently shaped retractor blades.

Figure 18A:
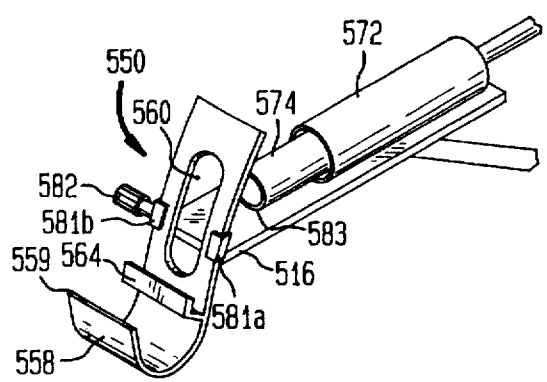
FIG. 18A is a partial perspective view of a drill guide and retractor having a retractor blade which is moveable superiorly and inferiorly with respect to the drill depth guide.
Figure 18B:
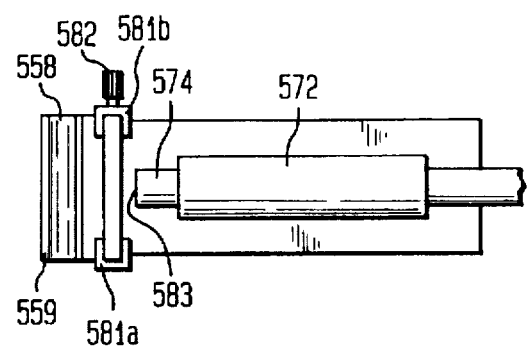
FIG. 18B is a top view of drill guide and retractor of FIG. 18A.

In all of the embodiments described above, the retractor may be moveable superiorly/inferiorly with respect to the drill guide. As seen in FIGS. 18A and 18B, a retractor blade 550 is provided at the end of a short leg 516 and is moveable with respect to a drill depth guide tip 583. The retractor blade 550 is connected to a short leg 516 (here, the outer sleeve 572 is mounted above the short leg 516) via a pair of C-shaped clamps 581A, 581B and may be slidably adjusted to a desired height with respect to the distal end of the inner sleeve 574 and then secured by a knurled screw 582. This structure is particularly suitable for use with fractures at the posterior region of the mandible. This is because the fracture may be at a location away from the bottom of the mandible under which the arcuate portion 558 of the retractor blade 550 is located. For example, if the fracture is located high on the ramus or condyle of the mandible, the arcuate portion tip 559 may be located relatively far from the fracture and therefore the retractor blade 550 is preferably moveable inferiorly with respect to the drill depth guide. A person skilled in the art recognizes that any number of structures may be used to slidably connect the retractor blade. This structure also allows the retractor blade to be demountable and interchangeable.

Figure 19A:
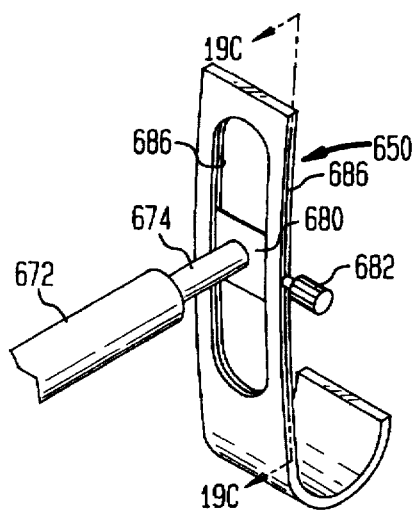
FIGS. 19A and 19B are partial perspective views of another embodiment of a drill guide and retractor having a retractor blade which is moveable superiorly and inferiorly with respect to the drill guide.
Figure 19B:
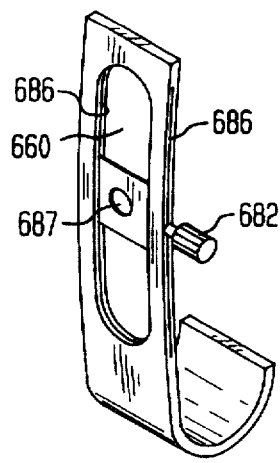
Figure 19C:
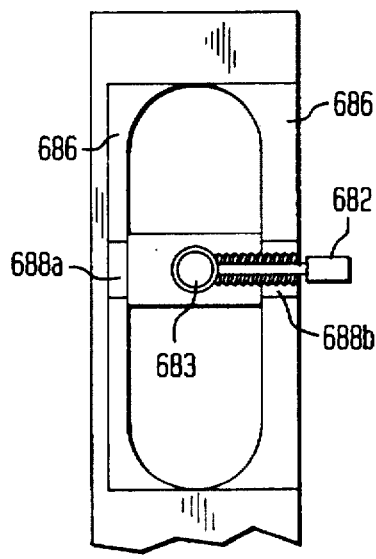
FIG. 19C is cross sectional view taken along lines 19C—19C of FIG. 19A.

FIGS. 19A, B, and C show an alternative embodiment of a retractor blade 650 which may be moved superiorly and inferiorly with respect to the drill depth guide. FIG. 19A shows the retractor blade 650 having a moveable drill guide-receiving sleeve 680 in the retractor blade aperture 660. The distal end of the inner sleeve 674 is received in an opening 684 in the receiving sleeve 680. The receiving sleeve 680 may then be tightened around a distal end of the inner sleeve 674 by screwing in knurled screw 682. The retractor blade 650 may be moved inferiorly or superiorly with respect to the drill guide by sliding the receiving sleeve 680 along a groove 686 in the retractor blade 650. The receiving sleeve 680 has side flanges 688A, 688B which extend into the groove 686 to slidably retain the sleeve 680. The groove 686 extends through the entire retractor blade 650 on the side having the knurled screw 682 as shown in FIG. 19C.

When the inner sleeve tip 683 is inserted in the hole 684, the screw 682 is tightened to hold the proximal end inner sleeve 674 within the receiving sleeve 680 and to press the side flange 688A against a wall of the groove to hold the retractor 650 in place in relation to the inner sleeve 674.

Figure 20A:
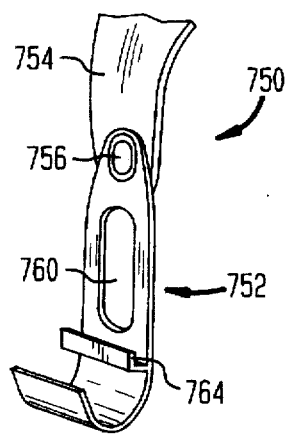
FIG. 20A is a perspective view of a retractor blade having a pivotal distal end.
Figure 20B:
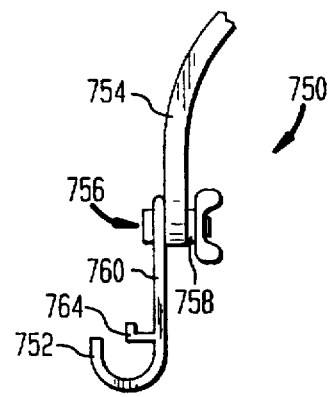
FIG. 20B is a side view of the retractor blade of FIG. 20A.
Figure 21A:
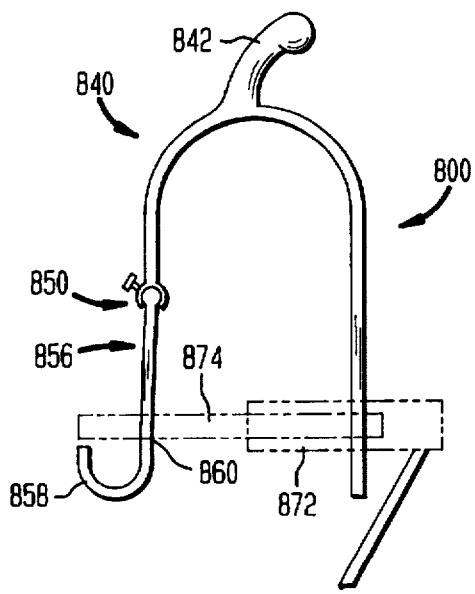
FIG. 21A is a side view of another embodiment of the drill guide and retractor according to the present invention.
Figure 21B:
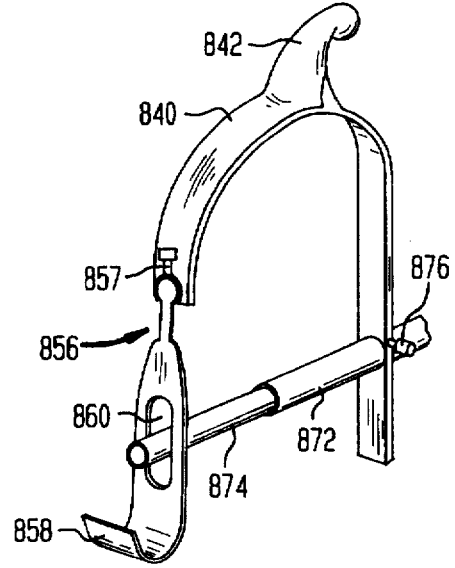
FIG. 21B is a perspective view of the drill guide and retractor of FIG. 21A.

FIGS. 20A and 20B illustrate a retractor blade 750 which has a distal end 752 which pivots with respect the proximal end of the retractor blade 754. The proximal and distal ends are connected by a swivel pin 756, which allows the distal end to radially rotate with respect the swivel pin 756 and proximal end 754. The swivel pin 756 may be secured to hold the distal end 752 in place by a locknut 758 which may be tighten to hold securely the proximal and distal ends together. Alternatively, the swivel pin 756 could be replaced with a universal joint 856, such as shown in FIGS. 21A and 21B. The universal joint 856 allows greater degrees of freedom and can be locked into place by screwing a set screw 857. The retractor blade 750 may include a bone plate shelf 764 located distally to an aperture 760.

FIGS. 21A and 21B show another embodiment of a retractor and drill depth guide according to the present invention. The retractor and drill depth guide 800 has an arched arm 840 which is connected to outer sleeve 872 which arches up and then down so that a retractor blade 850 having an aperture 860 aligns with inner sleeve 874.

This embodiment is particularly suitable for intraoral procedures because the arched arm 840 may extend upwards from the outer sleeve 872 outside of the patient and enter the patient through the mouth so that the retractor blade 850 may be located with the arcuate proximal portion 858 positioned under and behind the mandible. The arched arm 840 operates as a stabilizing arm located outside of the patient's mouth during the operation. The arched arm 840 may include a handle 842 to aid in retracting.

The arched arm may be fixedly connected to outer sleeve 872 as shown in FIG. 21A or may be demountably attached by loosening or tightening a screw 876 as shown in FIG. 21B. This retractor blade may include a swivel pin 856, bone plate shelf, or other features described above.

Figure 22:
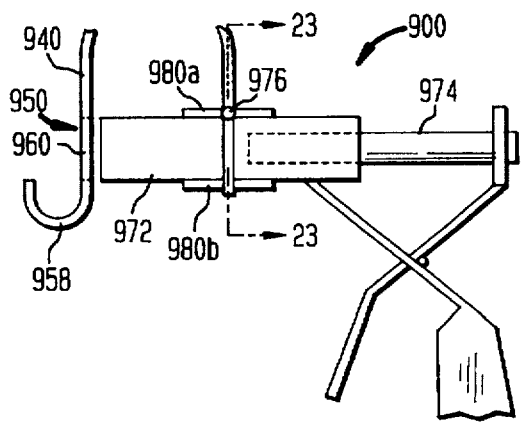
FIG. 22 is a side view of another embodiment of the drill guide and retractor according to the present invention.

FIG. 22 shows another embodiment of a retractor and drill depth guide having an arched arm. The retractor and drill depth guide 900 has an arched arm 940 which is demountably connected to outer sleeve 972 (FIG. 22 shows an adjustable length sleeve drill depth guide having the larger diameter outer sleeve 972 located distal to the smaller diameter inner sleeve 972, which, of course, is contemplated by the invention) in a manner which allows the arched arm, and therefore the retractor blade 950, to be moved anteriorly and posteriorly with respect to a distal end of the drill depth guide.

Figure 23:
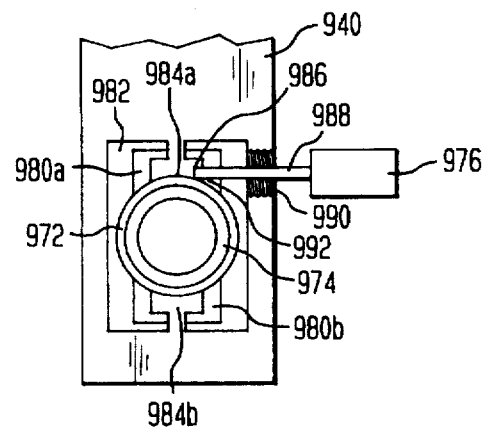
FIG. 23 is a cross sectional view taken along line 23–27 of FIG. 22.

As shown in FIGS. 22 and 23, the arched arm 940 is mounted on a set of tracks 980A, 980B which run longitudinally along the outer sleeve 972. An aperture 960 allows the arched arm 940 to fit over the drill depth guide. Complementary shaped tabs 984A, 984B slidably engage the tracks 980A, 980B. A threaded screw 976 rides along a slot 986 in one side of track 980B. Turning threaded screw 976 causes threaded portion 988 on the screw 976 to move in relation to a complementary threaded portion 990 in the arched arm so that a tip 992 of the screw contacts and retains tab 984A. A person skilled in the art will appreciate that any number of structures allow the arched arm to be moved anteriorly and posteriorly.

It will be apparent to those skilled in the art that the inventive surgical drill guide and retractor can also be used for wire fixation in addition to rigid internal fixation with a bone plate. A person skilled in the art will also appreciate that drill guide and retractor may also be used for procedures other than an ORIF and on bones other than the mandible.

The combination drill depth guide and retractors disclosed are preferably made of stainless steel or other material suitable for surgical use.

While the invention has been described by the reference to specific embodiments, this was for purposes of illustration only and should not be construed to limit the spirit or the scope of the invention.

I claim:

1. A surgical drill guide and retractor for restricting the penetration depth of a distal end of an instrument into a bone, a proximal end of the instrument having a larger girth than said distal end, said drill guide and retractor comprising:
   (a) an adjustable length sleeve, including:
      (1) an outer segment having a first lumen;
      (2) an inner segment having a second lumen, said inner segment being retractable disposed within said first lumen so that said first and second lumens are linearly aligned to form a single lumen of said adjustable length sleeve;
      (3) said inner and outer segments being cooperatively connected so that said inner sleeve is displaceable into and out of only a first end of said first lumen and so that a displacement of said inner segment out of and into said first lumen segment changes a longitudinal length of said adjustable length sleeve; and
      (4) said single lumen of said adjustable length sleeve having a diameter dimensioned for slidably receiving an instrument therethrough, until the larger girth proximal end of the instrument abuts a proximal end of said adjustable length sleeve and a distal end of the instrument protrudes from a distal end of said sleeve;

(b) a handle on said adjustable length sleeve, said handle including a trigger connected to the handle in a way to cause said inner segment to retract into said outer segment to shorten said adjustable length sleeve so as to expose a preselected length of the instrument;

wherein said penetration depth of said instrument is restricted to said preselected length; and (c) a retractor blade extending from a distal end of the adjustable length sleeve, the retractor blade including:
  (1) a curved portion at a proximal end of the adjustable length sleeve;
  (2) an arcuate portion having a tip, the arcuate portion connected to a distal end of the curved portion; and
  (3) an aperture defined in the retractor blade and located proximally from the tip;

wherein the retractor blade is slidably adjustable superiorly and inferiorly with respect to a distal end of the adjustable length sleeve and wherein a pair of clamps are connected to the distal end of the adjustable length sleeve for selectively retaining the retractor blade at a desired position.

2. The drill guide and retractor of claim 1, wherein the curved portion has a curvilinear shape defined to retract an incision parallel to a bone in a direction generally perpendicularly away from the bone.

3. The drill guide and retractor of claim 1, wherein the curved portion has a curvilinear shape defined to retract a lateral aspect of an incision parallel to a bone.

4. The drill guide and retractor of claim 1, wherein the arcuate tip has a substantially semicircular shape.

5. The drill guide and retractor of claim 1, wherein the retractor blade further includes a bone plate carrying shelf connected to the retracting blade distally of the aperture.

6. The drill guide and retractor of claim 5, wherein the bone plate carrying shelf is shaped to snugly hold a bone plate.

7. The drill guide and retractor of claim 1, wherein said adjustable length sleeve further comprises biasing means for biasing said inner segment into an extended position from said outer segment.

8. The drill guide and retractor of claim 1, wherein said trigger is cooperatively attached to said adjustable length sleeve for sliding movement with said handle and said adjustable length sleeve.

9. The drill guide and retractor of claim 8, wherein said trigger comprises a long member and an eyelet connected to said long member, said long member being attached to said adjustable length sleeve with said eyelet extending towards said handle.

10. The drill guide and retractor of claim 1, wherein the retractor blade is demountably attached to the adjustable length sleeve.

11. The drill guide and retractor of claim 1, wherein the distal end of the first sleeve is selectively connected to a moveable drill guide-receiving sleeve.

12. The drill guide and retractor of claim 11, wherein the drill guide-receiving sleeve has side flanges for slidably engaging a groove in the retractor blade.

13. The drill guide and retractor of claim 11 further including a screw connected to the drill guide receiving sleeve for selectively retaining the distal end of the first sleeve and the drill guide-receiving sleeve.

14. A surgical drill guide and retractor for restricting the penetration depth of a distal end of an instrument into a bone, a proximal end of the instrument having a larger girth than said distal end, said drill guide and retractor comprising:

(a) an adjustable length sleeve, including:
  (1) an outer segment having a first lumen;
  (2) an inner segment having a second lumen, said inner segment being retractable disposed within said first lumen so that said first and second lumens are linearly aligned to form a single lumen of said adjustable length sleeve;
  (3) said inner and outer segments being cooperatively connected so that said inner sleeve is displaceable into and out of only a first end of said first lumen and so that a displacement of said inner segment out of and into said first lumen segment changes a longitudinal length of said adjustable length sleeve; and
  (4) said single lumen of said adjustable length sleeve having a diameter dimensioned for slidably receiving an instrument therethrough, until the larger girth proximal end of the instrument abuts a proximal end of said adjustable length sleeve and a distal end of the instrument protrudes from a distal end of said sleeve;

(b) a handle on said adjustable length sleeve, said handle including a trigger connected to the handle in a way to cause said inner segment to retract into said outer segment to shorten said adjustable length sleeve so as to expose a preselected length of the instrument;

wherein said penetration depth of said instrument into said hole is restricted to said preselected length; and (c) a retractor blade extending from a distal end of the adjustable length sleeve, the retractor blade including:
  (1) a curved portion at a proximal end of the adjustable length sleeve;
  (2) an arcuate portion having a tip, the arcuate portion connected to a distal end of the curved portion; and
  (3) an aperture defined in the retractor blade and located proximally from the tip;

wherein the retractor blade includes a joint pivotally connecting proximal and distal ends of the retractor blade.

15. The drill guide and retractor of claim 14, wherein the joint is a swivel pin.

16. The drill guide and retractor of claim 14, wherein the joint is a universal joint.

* * * * *